United States Patent
Wirth

(10) Patent No.: US 10,185,040 B2
(45) Date of Patent: Jan. 22, 2019

(54) DETECTOR APPARATUS WITH DETACHABLE EVALUATION UNIT

(71) Applicant: Siemens Healthcare GmbH, Erlangen (DE)

(72) Inventor: Stefan Wirth, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/459,426

(22) Filed: Mar. 15, 2017

(65) Prior Publication Data

US 2017/0269236 A1 Sep. 21, 2017

(30) Foreign Application Priority Data

Mar. 17, 2016 (DE) .......................... 10 2016 204 457

(51) Int. Cl.
| | |
|---|---|
| *G01T 1/20* | (2006.01) |
| *A61B 6/03* | (2006.01) |
| *A61B 6/00* | (2006.01) |
| *G01T 1/29* | (2006.01) |

(52) U.S. Cl.
CPC ............ *G01T 1/2006* (2013.01); *A61B 6/032* (2013.01); *A61B 6/035* (2013.01); *A61B 6/4233* (2013.01); *A61B 6/4291* (2013.01); *G01T 1/2018* (2013.01); *G01T 1/2985* (2013.01)

(58) Field of Classification Search
CPC ....... A61B 6/032; A61B 6/035; A61B 6/4233; G01T 1/2006; G01T 1/2018; G01T 1/2985

USPC .......... 250/370.09, 370.11, 366, 367, 361 R, 250/363.01; 378/19, 98.8, 21, 4
See application file for complete search history.

(56) References Cited

U.S. PATENT DOCUMENTS

| | | | | |
|---|---|---|---|---|
| 4,338,521 A | * | 7/1982 | Shaw | G01T 1/2018 250/367 |
| 4,429,227 A | | 1/1984 | DiBianca | |
| 4,629,893 A | * | 12/1986 | Hanz | G01T 1/1648 250/363.1 |
| 5,059,798 A | * | 10/1991 | Persyk | G01T 1/20 250/363.02 |
| 6,794,672 B2 | * | 9/2004 | Sklebitz | G03B 42/02 250/214 VT |
| 2002/0064252 A1 | * | 5/2002 | Igarashi | A61B 6/06 378/19 |

(Continued)

FOREIGN PATENT DOCUMENTS

DE 3247204 A1 7/1983

*Primary Examiner* — David Porta
*Assistant Examiner* — Blake Riddick
(74) *Attorney, Agent, or Firm* — Harness, Dickey & Pierce, P.L.C.

(57) ABSTRACT

A detector apparatus includes a scattered radiation grid; a scintillator unit for converting X-rays into a light quantity; an evaluation unit for converting the light quantity into electric signals; and a module-receiving appliance. The scintillator unit and the scattered radiation grid are mechanically connected to the module-receiving appliance via a first connection and the evaluation unit is mechanically connected to the module-receiving appliance via a second connection, independent of the first connection. The evaluation unit, the scintillator unit and the scattered radiation grid are aligned with respect to one another such that light quantity, when emitted from sub-regions of the scintillator unit, is registered by sub-regions of the evaluation unit.

18 Claims, 6 Drawing Sheets

(56) References Cited

U.S. PATENT DOCUMENTS

| | | | |
|---|---|---|---|
| 2005/0035294 A1 | 2/2005 | Leppert | |
| 2008/0049892 A1* | 2/2008 | Maltz | A61B 6/4233 378/19 |
| 2011/0255658 A1* | 10/2011 | Matsuda | A61B 6/032 378/19 |
| 2011/0278463 A1 | 11/2011 | Miess | |
| 2012/0132834 A1 | 5/2012 | Freund | |
| 2016/0327655 A1* | 11/2016 | Hartmann | G01T 1/20 |
| 2017/0010366 A1* | 1/2017 | Schroeter | G01T 1/208 |
| 2017/0254907 A1* | 9/2017 | Ergler | G01T 1/18 |

* cited by examiner

DETECTOR APPARATUS WITH DETACHABLE EVALUATION UNIT

PRIORITY STATEMENT

The present application hereby claims priority under 35 U.S.C. § 119 to German patent application number DE 102016204457.5 filed Mar. 17, 2016, the entire contents of which are hereby incorporated herein by reference.

FIELD

At least one embodiment of the invention generally relates to a detector apparatus and a medical device, wherein the scintillator unit is connected to the evaluation unit such that the scintillator unit can be fixed in the detector apparatus independently of the evaluation unit.

BACKGROUND

Integrated indirectly-converting X-ray detectors can be used in X-ray imaging, for example in computed tomography, angiography or radiography. The X-rays or photons can be converted in indirectly-converting X-ray detectors into light by a suitable converter material and into electric pulses by way of photodiodes. Frequently scintillators, for example GOS ($Gd_2O_2S$), CsJ, YGO or LuTAG are used as the converter material. Scintillators are in particular used in medical X-ray imaging in the energy range of up to 1 MeV.

So-called indirectly-converting X-ray detectors, so-called scintillator detectors, are typically used in which the X-rays or gamma rays are converted into electric signals in two stages. In a first stage, the X-ray or gamma quanta are absorbed in a sub-region of the scintillator unit and converted into optical visible light, a light quantity; this effect is called luminescence. The light excited by luminescence is then converted in a second stage by a first photodiode optically coupled to the scintillator unit in a sub-region of an evaluation unit into an electric signal, read out via an electronic evaluation or readout device and then forwarded to a computing unit.

The sub-regions of the scintillator unit and the evaluation unit are as a rule subdivided such that a sub-region of the evaluation unit is assigned to each sub-region of the scintillator unit. This is then referred to as a pixelated X-ray detector. X-ray detectors such as those used in computed tomography, for example, are typically made up of a plurality of modules, which comprise a scattered radiation grid, a scintillator unit, an evaluation unit with photosensors or photodiodes, for example as a photodiode array, and with electronic units for converting the analog signal into digital information and a mechanical carrier. The scattered radiation grid is used to suppress scattered radiation. The mechanical carrier is used to mount the scattered radiation grid, the scintillator unit and the evaluation unit. The scattered radiation grid, scintillator unit and photodiode are typically pixelated in the same way in two directions, for example into rectangular or square pixels. In order to achieve good dose utilization and simultaneously low crosstalk between the pixels, the scattered radiation grid, scintillator unit and photodiode are positioned very exactly with respect to one another when assembling the modules.

When assembling the modules, the scintillator unit or the scintillator array are permanently attached to the photodiode array with the aid of an optical adhesive and aligned at the same time. Both are then secured together on the mechanical carrier or the mechanical module unit. The scattered radiation grid is then also permanently connected to the module, either by bonding with the scintillator array or by way of mechanical fixation on the mechanical carrier, wherein once again optimal positioning with respect to the scintillator array is to be achieved. Finally, the modules pre-assembled in this way are secured in the housing of the detector or the module-receiving appliance. In this case, suitable measures, for example stop surfaces, locating pins or the like ensure that the grip openings of the scattered radiation grid are aligned as well as possible with the tube focus.

Publication DE 102010062192 B3 discloses a 2D collimator for a radiation detector with 2D collimator modules arranged in series, wherein adjacent 2D collimator modules are glued together to establish a fixed mechanical connection to facing module sides and wherein, on their free-remaining side, the outer 2D collimator modules have a retaining element for mounting the 2D collimator opposite a detector mechanism.

Publication DE 102010020610 A1 discloses a radiation detector comprising a scintillator with septa for separating scintillator elements arranged alongside one another and a collimator with webs for forming laterally enclosed radiation channels, wherein the webs are inserted into the septa in order to avoid crosstalk between adjacent scintillator elements.

Publication DE 10335125 B4 discloses a method for producing a luminescent body for an X-ray detector, in particular for X-ray computed tomography scanners, which is made of a ceramic with the general composition $(M_{1-x}Ln_x)_2O_2S$, M being at least one element selected from the group: Y, La, Sc, Lu and/or Gd, and Ln being at least one element selected from the group: Eu, Ce, Pr, Tb, Yb, Dy, Sm and/or Ho.

SUMMARY

The inventors have recognized a problem that the scintillator unit and the evaluation unit are inseparably connected so that, for example, when the evaluation unit is replaced, it is also necessary to replace the scintillator unit.

At least one embodiment of the invention discloses a detector apparatus and a medical device, which facilitate simplified repair and maintenance.

At least one embodiment of the invention is directed to a detector apparatus; and at least one embodiment of the invention is directed to a medical device.

At least one embodiment of the invention relates to a detector apparatus comprising a scattered radiation grid, a scintillator unit for converting X-rays into a light quantity, an evaluation unit for converting the light quantity into electric signals, and a module-receiving appliance. The scintillator unit and the scattered radiation grid are mechanically connected to the module-receiving appliance via a first connection. The evaluation unit is mechanically connected to the module-receiving appliance via a second connection which is independent of the first connection. The evaluation unit, the scintillator unit and the scattered radiation grid are aligned with respect to one another such that the light quantity emitted from sub-regions of the scintillator unit is registered by sub-regions of the evaluation unit.

At least one embodiment of the invention further relates to a medical device comprising a detector apparatus according to the invention. At least one embodiment of the invention, the medical device is a computed tomography scanner. The advantages of the detector apparatus according to at least one embodiment of the invention can be transferred to the medical device. The detector apparatus for the medical device can advantageously be produced less expensively. Repairs to the detector apparatus can advantageously be less expensive.

BRIEF DESCRIPTION OF THE DRAWINGS

The following explains example embodiments of the invention in more detail with reference to the drawings, which show.

DETAILED DESCRIPTION OF THE EXAMPLE EMBODIMENTS

Figure 1:
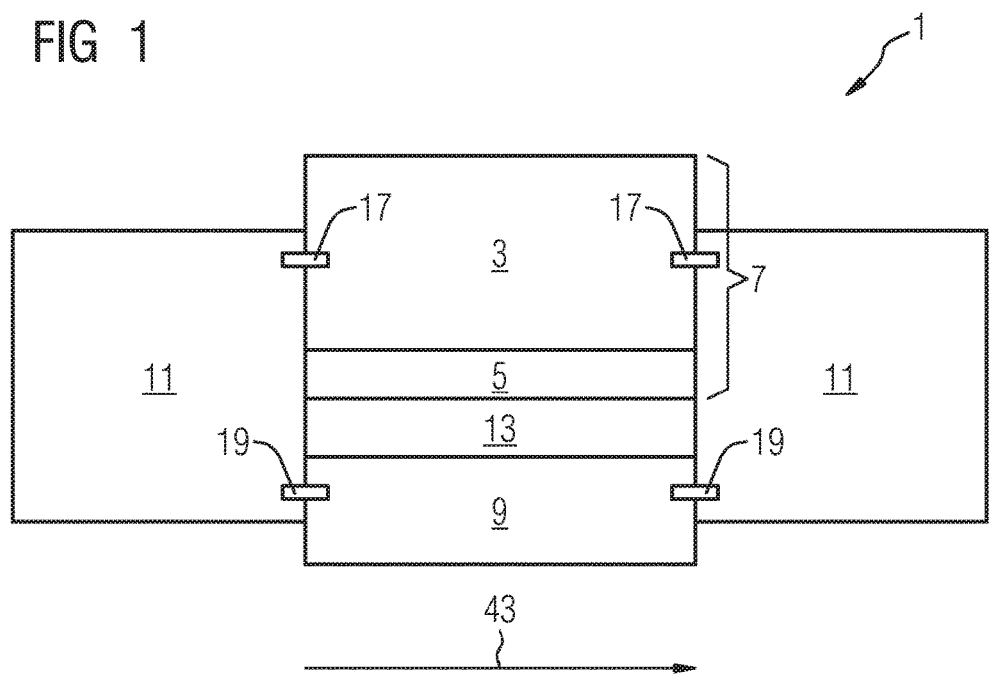
FIG. 1 a schematic view of a detector apparatus according to the invention in a first embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a detector apparatus comprising a scattered radiation grid, a scintillator unit for converting X-rays into a light quantity, an evaluation unit for converting the light quantity into electric signals, and a module-receiving appliance. The scintillator unit and the scattered radiation grid are mechanically connected to the module-receiving appliance via a first connection. The evaluation unit is mechanically connected to the module-receiving appliance via a second connection which is independent of the first connection. The evaluation unit, the scintillator unit and the scattered radiation grid are aligned with respect to one another such that the light quantity emitted from sub-regions of the scintillator unit is registered by sub-regions of the evaluation unit.

In at least one embodiment, the scattered radiation grid can comprise grid walls or grid openings aligned to focus a radiation source. The grid walls can be stepped. The grid openings can be conical or in the shape of a truncated pyramid. The grid openings can have a square or rectangular base. The scattered radiation grid comprises an absorption material suitable for absorbing X-rays, for example lead or tungsten. The scattered radiation grid can be in one piece.

In at least one embodiment, the scintillator unit comprises sub-regions. The sub-regions can, for example, be defined by septa filled with a reflector material. The sub-regions can also be defined by the alignment or assignment to the scattered radiation grid. The sub-region can be a detector element or a pixel.

In at least one embodiment, the evaluation unit can comprise a photodiode or a photodiode array and an electronic evaluation unit. The evaluation unit can comprise a mechanical carrier or a mechanical module unit. Further electronic readout and/or evaluation units can be arranged on the mechanical carrier. The evaluation unit can be connected to the module-receiving appliance by way of a second connection.

In at least one embodiment, the module-receiving appliance can, for example, be embodied as a bent, module-receiving appliance with a recess as a detector window. A plurality of scattered radiation grids, scintillator units and evaluation units can be arranged in the recess. The scattered radiation grid, scintillator unit and evaluation unit can in particular be fixed in the direction of rotation on the module-receiving appliance.

In at least one embodiment, the module-receiving appliance can also be a mechanical carrier on which the scattered radiation grid, scintillator unit and/or evaluation unit can be fixed. It is possible for a plurality of mechanical carriers to be provided, for example one mechanical carrier for the scattered radiation grid and one mechanical carrier for the evaluation unit. The mechanical carrier can be fixed to the module-receiving appliance. The mechanical carrier can be comprised by the module-receiving appliance. The mechanical connection can be formed by screws, locating pins, locating holes or the like. In addition, it is possible for a groove, a spring or a similarly embodied positive and negative shape to be used for the mechanical connection or alignment.

X-rays pass through a grid opening of the scattered radiation grid and land on a sub-region of the scintillator unit. In the scintillator unit, the X-rays are converted into a first light quantity. The sub-region of the scintillator unit emits a light quantity, preferably the first light quantity, or the light quantity is coupled out of the scintillator unit. The light quantity lands on a sub-region of the evaluation unit. The light quantity can be registered by the sub-region of the evaluation unit.

The alignment of the sub-region of the scintillator unit with the sub-region of the evaluation unit can, for example, be embodied such that the two-dimensional orientation of the sub-regions overlaps or corresponds at least partially, preferably exactly. The surface normals of the sub-region of the scintillator unit and the evaluation unit can preferably be parallel. The surface normal can, for example, for a sub-region in the center of the scintillator unit, a sub-region in the center of the evaluation unit or the scintillator array, point in the direction of the radiation source. For sub-regions outside the center of the scintillator unit or the evaluation unit, the surface normal can point approximately, but not exactly, in the direction of the radiation source.

The sub-region of the scintillator unit and the sub-region of the evaluation unit can have a similar or the same two-dimensional extension. There can be a gap between the sub-region of the scintillator unit and the sub-region of the evaluation unit. The gap can be air-filled or filled with an optical filler.

The first connection and/or the second connection can be fixing device. The first connection and the second connection are independent of one another. There can be a further connection between the detection unit formed by the scintillator unit and the scattered radiation grid and the evaluation unit, for example in form of a locating pin, locating hole, groove, spring or the like. The further connection can in particular be used for the mutual alignment of the evaluation unit and the detection unit.

The inventors suggest, in at least one embodiment, a modification of the construction of a detector apparatus compared to known detector apparatuses. The scattered radiation grid can be mechanically connected to the module-receiving appliance via a first connection, for example, in a fixed or reversible manner. The scattered radiation grid can be produced in the form of modules, large segments or as one piece. With mechanical connection or fixing, it is also possible for the grid openings to be aligned with the tube focus or the radiation source. The scintillator unit can preferably be mechanically connected to the scattered radiation grid.

Jointly with the scattered radiation grid, the scintillator unit is no longer connected in a fixed and inseparable way to the evaluation unit or the photodiode array. The module-receiving appliance, the scattered radiation grid and the scintillator unit advantageously form a mechanically stable unit that can remain unchanged after the first assembly.

Advantageously, the bonding process between the scintillator unit and evaluation unit using special optical adhesives can be dispensed with. As individual components, the scattered radiation grid, the scintillator unit and the evaluation unit can advantageously have different sizes, thus enabling, for example, area-related efficiency to be optimized in the individual production processes. If the evaluation unit is replaced due to electronic failures, advantageously, there is no longer any risk of the scattered radiation grid being damaged. The replacement of the evaluation unit can advantageously be less expensive since now only the evaluation unit is replaced. Advantageously, on the replacement of evaluation units, it is no longer necessary to pay attention to sorting according to scintillator properties; in particular, when replacing central evaluation units, the time-consuming "re-setting" of adjacent evaluation units in order to ensure equivalent scintillator properties after the replacement and the installation of new evaluation units at the edge is no longer necessary.

According to one embodiment of the invention, the first connection and/or the second connection is a detachable connection. The detachable connection can be formed by an indirect connection via the first connection and the second connection to the module-receiving appliance.

Detachable can mean non-destructive, repeatedly detachable or re-connectable. Detachable can mean that no special tool or no special conditions, for example temperature, chemical bath or the like is required to detach the connection. Detachable can mean that the connection can advantageously be detached simply and quickly by a service technician. Detachable can mean that, in fixed condition, the connection is permanently mechanically stable.

According to one embodiment of the invention, the scintillator unit forms a detection unit with the scattered radiation grid. The scintillator unit can be connected to the scattered radiation grid. The detection unit can be mechanically connected to the module-receiving appliance via the first connection. The scintillator unit and scattered radiation grid can advantageously be jointly mechanically connected to the module-receiving appliance via the first connection. The scintillator unit and scattered radiation grid can advantageously be mechanically connected to one another and aligned in one step before the mechanical connection to the module-receiving appliance.

According to one embodiment of the invention, the detection unit and the evaluation unit have different two-dimensional extensions. The surface normals of the detector surface or the surface of the detection unit can preferably point toward the radiation source. The detector surface and the evaluation unit can have a two-dimensional extension approximately in the direction of rotation and phi-direction. The two-dimensional extension can in particular be a flat two-dimensional extension. The detection unit and the evaluation unit can advantageously be produced in extensions which can be produced with good reproducibility during production.

According to one embodiment of the invention, the detection unit is assigned to a plurality of evaluation units. The evaluation units can advantageously have smaller two-dimensional extensions than the detection unit. The replacement of an evaluation unit can advantageously be less expensive due to the smaller two-dimensional extension.

According to one embodiment of the invention, one sub-region of the scintillator unit is assigned to a cell of the scattered radiation grid. The sub-region of the scintillator unit can be assigned to a grid opening of the scattered radiation grid. The cell of a scattered radiation grid can be the surface of the grid opening on the side facing the scintillator unit and have half the thickness or surface of the adjacent grid walls. The sub-region, in particular an active sub-region, can have a two-dimensional extension corresponding to at least the surface of the grid opening. It is, for example, possible, for septa filled with reflector material to be provided below the grid walls. The sub-region can also be active below the grid walls. An assignment of the grid opening to the sub-region of the scintillator unit can advantageously be achieved.

According to one embodiment of the invention, the sub-region of the scintillator unit and the cell of the scattered radiation grid have the same two-dimensional extension. The scintillator unit can be subdivided into sub-regions corresponding to the cell size of the scattered radiation grid. This can correspond to the pixelation of the detector. The connection of the scintillator unit and the scattered radiation grid is preferably as exact as possible. An unambiguous assignment of the sub-region of the scintillator unit to a cell or a grid opening of the scattered radiation grid can advantageously be achieved.

According to one embodiment of the invention, the sub-region of the scintillator unit is arranged in a grid opening of the scattered radiation grid. The sub-region of the scintillator unit can be formed as a cube-shaped or square scintillator element. The assignment of the sub-region of the scintillator unit and a grid opening of the scattered radiation grid is advantageously unambiguous. Faulty adjustment or misalignment of the sub-region of the scintillator unit and the grid opening of the scattered radiation grid can advantageously be avoided.

According to one embodiment of the invention, the scintillator unit comprises, for example, GOS, YGO, BGO, LUTAG, CsI, YAG or GGAG. The scintillator unit can advantageously be produced with a two-dimensional extension.

According to one embodiment of the invention, the sub-region of the scintillator unit comprises a plurality of needle-shaped scintillator elements. The scintillator unit can consist of a plurality of thin scintillator needles that can be packed together as tightly as possible and which have a cross section that can be substantially smaller than the sub-region of the scintillator unit or the sub-region of the scattered radiation grid. Advantageously, the requirements for exact alignment of the scattered radiation grid, the scintillator unit and the evaluation unit are lower.

According to one embodiment of the invention, the scintillator elements comprise, for example, GOS, YGO, BGO, LUTAG, CsI, YAG or GGAG. The scintillator elements can advantageously be produced in a needle shape. At the same time, the needle-shaped scintillator elements can be arranged perpendicular to the detector surface or two-dimensional extension of the scintillator unit.

According to one embodiment of the invention, a gap is formed between the scintillator unit and the evaluation unit. A gap can remain between the scintillator unit and the evaluation unit. The height of the gap or the distance between the scintillator unit and evaluation unit can range from a few micrometers to a few millimeters. The scintillator unit and the evaluation unit can advantageously be mechanically decoupled.

According to one embodiment of the invention, the gap is filled with a fluid. The fluid can be a gas, a liquid or a gel. The gas can, for example, be air. The light quantity emitted from the sub-region of the scintillator unit can advantageously land on the sub-region of the evaluation unit while subject to as little influence as possible.

According to one embodiment of the invention, the gap is filled with an optical filler. The optical filler can be transparent to the light quantity. The optical filler can be a gel or a pad. The light quantity emitted from the sub-region of the scintillator element can advantageously land on the sub-region of the evaluation unit while subject to as little influence as possible. The transportation of the light from the sub-region of the scintillator unit to the sub-region of the evaluation unit in the gap can advantageously be optimized.

According to one embodiment of the invention, the scintillator unit and/or the evaluation unit comprises a fixing device. The fixing device can be the first connection or the second connection. The fixing device can be formed by an enlargement of the extension of the scintillator unit or the evaluation unit beyond the region used for the detection of X-rays. The fixing device can, for example, comprise locating holes, locating pins or drill holes for fixing via screws.

At least one embodiment of the invention further relates to a medical device comprising a detector apparatus according to the invention. At least one embodiment of the invention, the medical device is a computed tomography scanner. The advantages of the detector apparatus according to at least one embodiment of the invention can be transferred to the medical device. The detector apparatus for the medical device can advantageously be produced less expensively. Repairs to the detector apparatus can advantageously be less expensive.

FIG. 1 shows an example embodiment of the detector apparatus according to the invention 1 in a first embodiment. The detector apparatus 1 comprises a scattered radiation grid 3, a scintillator unit 5 for converting X-rays into a light quantity, an evaluation unit 9 for converting the light quantity into electric signals and a module-receiving appliance 11. The scintillator unit 5 and the scattered radiation grid 3 are mechanically connected to the module-receiving appliance 11 via a first connection 17. The evaluation unit 9 is mechanically connected to the module-receiving appliance 11 via a second connection 19 which is independent of the first connection 17. The module-receiving appliance 11 is embodied such that a detector window is parallel to the axis of rotation 43 and the detection unit 7 and the evaluation unit 9 are arranged in the detector window.

The evaluation unit 9, the scintillator unit 5 and the scattered radiation grid 3 are aligned with respect to one another such that the light quantity emitted from the sub-regions of the scintillator unit 5 is registered by sub-regions of the evaluation unit 9. A gap 13 is formed between the scintillator unit 5 and the evaluation unit 9. The scintillator unit 5 forms a detection unit 7 with the scattered radiation grid 3. The indirect connection between the detection unit 7 and evaluation unit 9 via the first connection 17 and the second connection 19 to the module-receiving appliance 11 is detachable. The scintillator unit 5 comprises, for example, GOS, YGO, BGO, LUTAG, CsI, YAG or GGAG. The gap 13 can be air-filled or filled with an optical filler.

Figure 2:
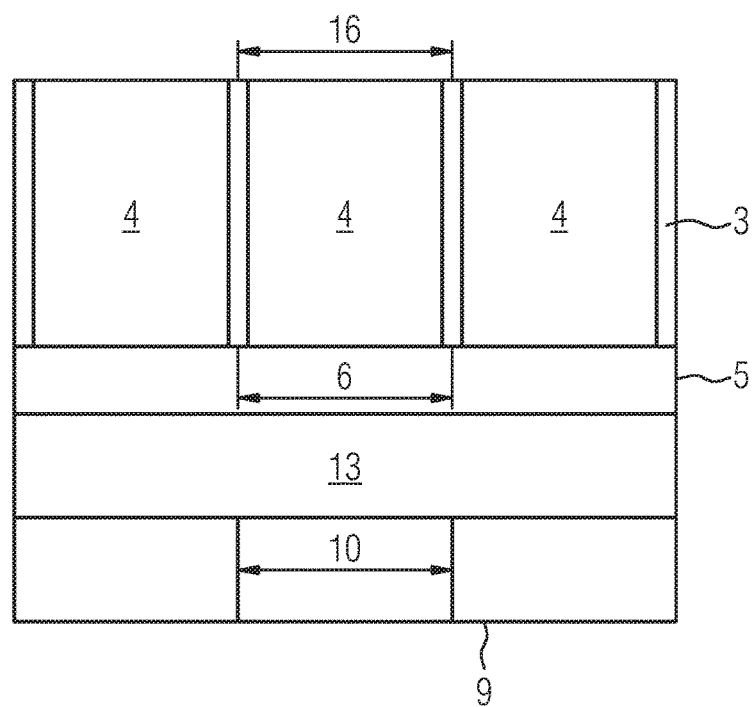
FIG. 2 a schematic view of an arrangement of the scattered radiation grid, scintillator unit and evaluation unit according to the invention in a first embodiment.

FIG. 2 shows an example embodiment of the arrangement of the scattered radiation grid 3, scintillator unit 5 and evaluation unit 9 according to the invention in a first embodiment. The scattered radiation grid 3 comprises, for example, three grid openings 4. The scattered radiation grid 3 comprises cells 16 corresponding to an extension of the grid opening 4 and twice half the wall thickness. The extensions of the sub-region 6 of the scintillator unit 5 and the sub-region 10 of evaluation unit 9 correspond to the cell 16. In a further embodiment the, in particular active, sub-region 10 of the evaluation unit 9 can be smaller than the sub-region 6 of the scintillator unit 5, for example due to the arrangement of guard rings or protective rings in the evaluation unit.

Figure 3:
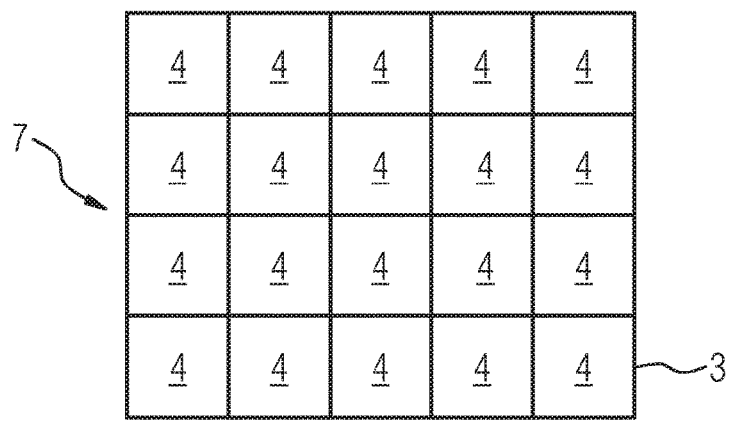
FIG. 3 a schematic view of a according to the invention detection unit in a first embodiment.

FIG. 3 shows an example embodiment of the detection unit 7 according to the invention in a first embodiment in a top view. The top view is depicted from the direction of view from the radiation source to the detector apparatus. The top view shows the scattered radiation grid 3 with grid openings 4. In the direction of view of the top view, the sub-regions of the scintillator unit are located behind the grid openings 4.

Figure 4:
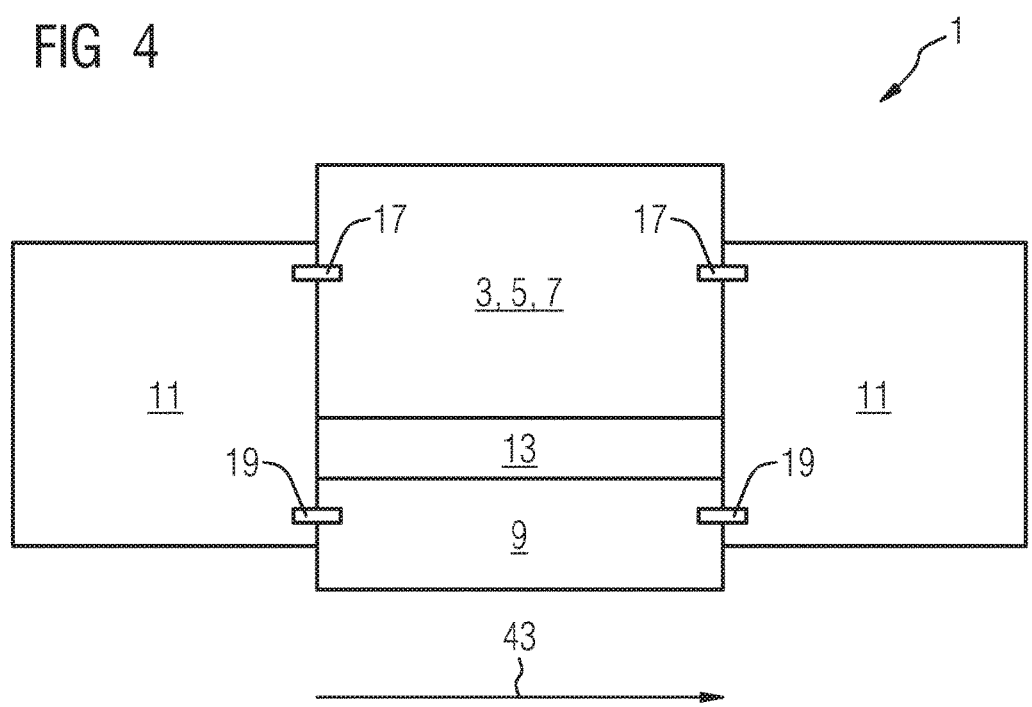
FIG. 4 a schematic view of a detector apparatus according to the invention in a second embodiment.

FIG. 4 shows an example embodiment of the detector apparatus according to the invention 1 in a second embodiment. The second embodiment differs from the first embodiment of the detector apparatus 1 in that that the scintillator unit 5 is embodied within the scattered radiation grid 3.

Figure 5:
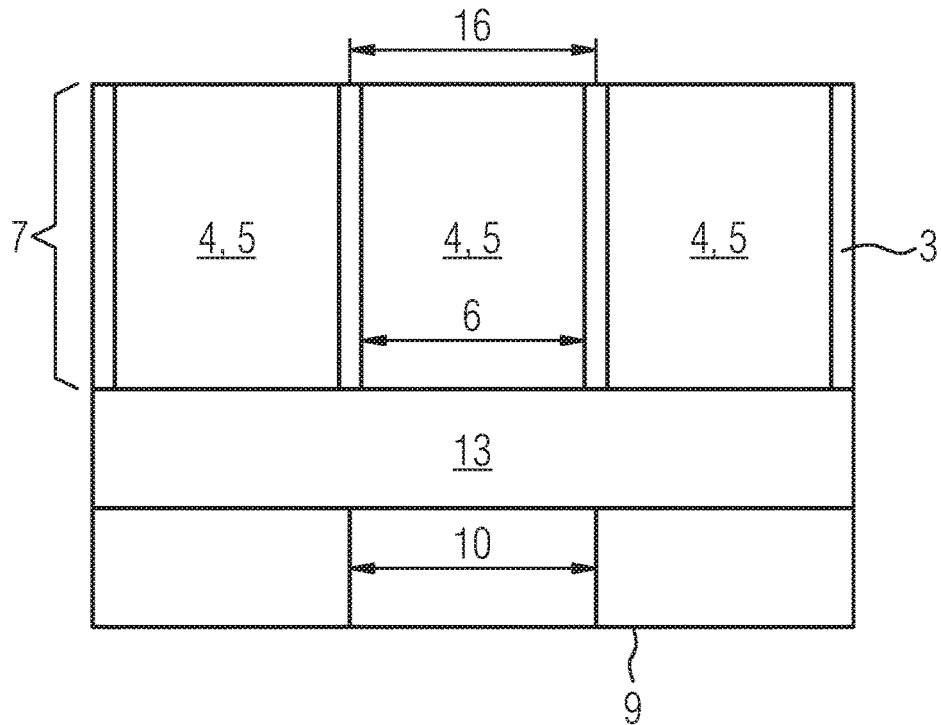
FIG. 5 a schematic view of an arrangement of the scattered radiation grid, scintillator unit and evaluation unit according to the invention in a second embodiment.

FIG. 5 shows an example embodiment of the arrangement of the scattered radiation grid, scintillator unit and evaluation unit according to the invention in a second embodiment. The sub-region 6 of the scintillator unit 5 is embodied in a grid opening 4 of the scattered radiation grid. The cube-shaped or square scintillator element extends as far as the grid walls; the height of the scintillator element is preferably less than the slot height of the grid opening.

Figure 6:
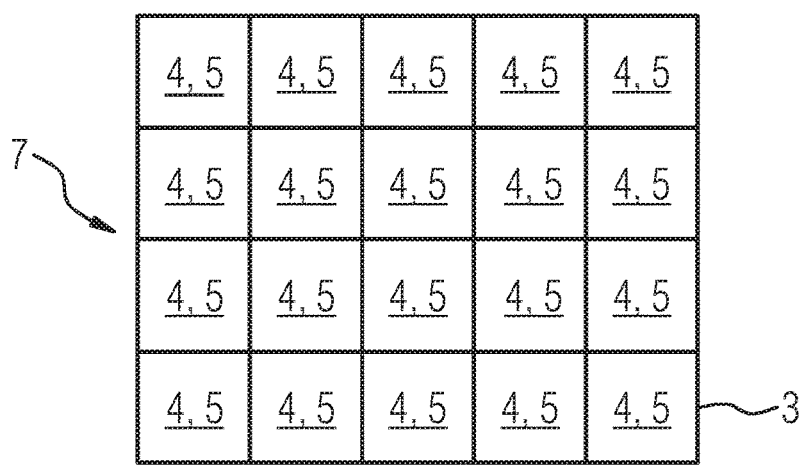
FIG. 6 a schematic view of a detection unit according to the invention in a second embodiment.

FIG. 6 shows an example embodiment of the detection unit 7 according to the invention in a second embodiment in a top view. The second embodiment differs from the first embodiment of the detection unit 7 in that that the scintillator unit 5 is embodied within the grid openings 4 of the scattered radiation grid 3.

Figure 7:
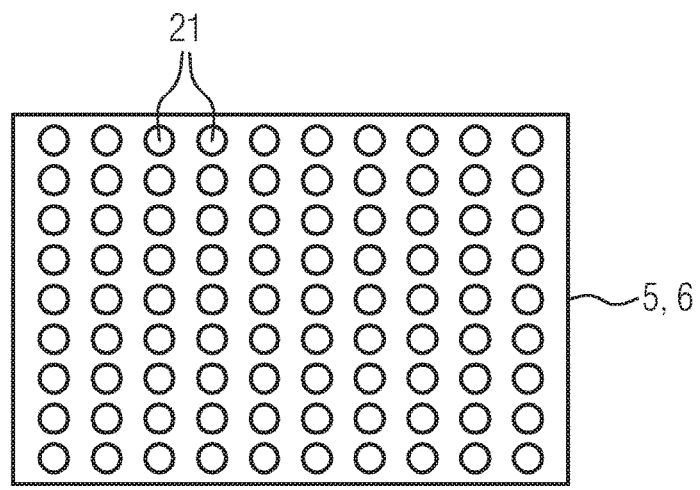
FIG. 7 a schematic view of a sub-region of a scintillator unit according to the invention.

FIG. 7 shows an example embodiment of the sub-region 6 of a scintillator unit 5 according to the invention. The sub-region 6 of the scintillator unit 5 comprises a plurality of needle-shaped scintillator elements 21. The scintillator unit 5 consists of a plurality of thin scintillator needles that are packed together as tightly as possible and which have a cross section that is substantially smaller than the sub-region 6 of the scintillator unit 5 or the grid opening 4 of the scattered radiation grid 3. The needle-shaped scintillator elements 21 comprise, for example, GOS, YGO, BGO, LUTAG, CsI, YAG or GGAG. The scintillator elements 21 can be arranged regularly or irregularly. Individual scintillator elements 21 can also be located in the marginal region of the sub-region 6 and overlap an adjacent sub-region.

Figure 8:
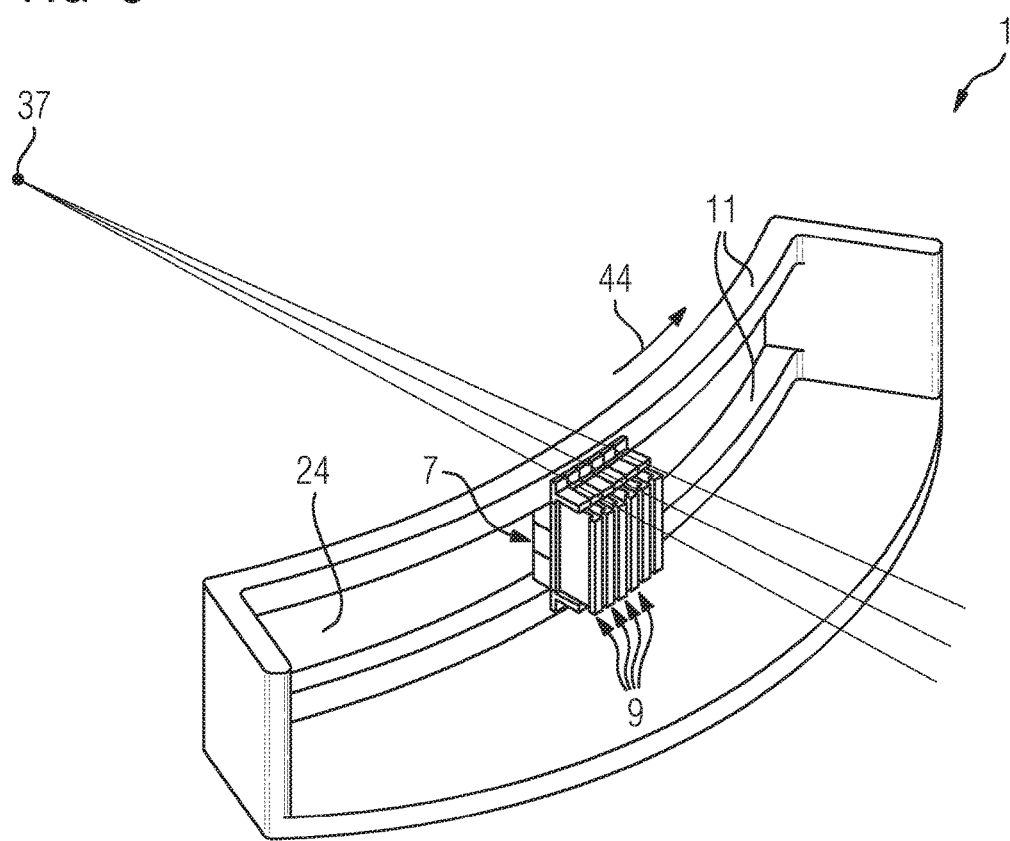
FIG. 8 a schematic view of a detector apparatus according to the invention according to a third embodiment.

FIG. 8 shows an example embodiment of the detector apparatus according to the invention 1 according to a third embodiment. The detector apparatus 1 comprises a module-receiving appliance 11. In the module-receiving appliance 11, a plurality of evaluation units 9 and detection units 7 are arranged in a detector window 24 along the phi-direction 44. The X-rays are emitted from the radiation source 37 and land on the detection units 7. The direction of the X-rays is indicated by the lines emerging from the radiation source 37.

Figure 9:
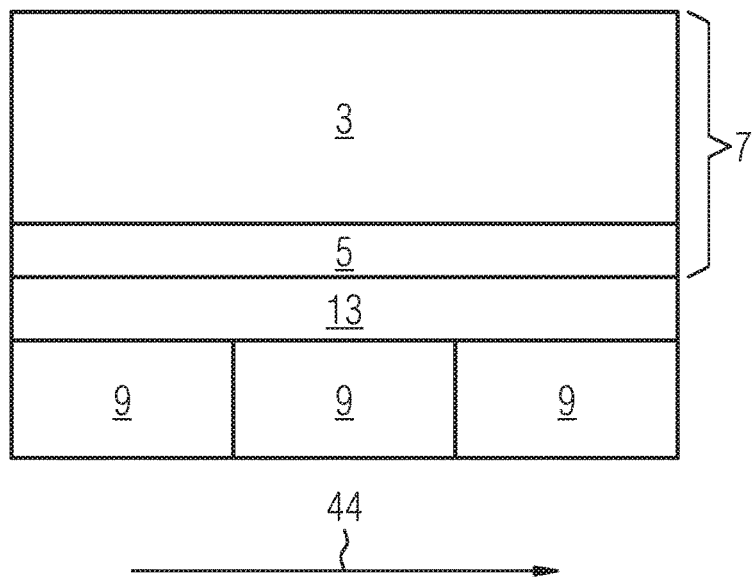
FIG. 9 a schematic view of a according to the invention arrangement of the scattered radiation grid, scintillator unit and evaluation unit in a third embodiment.

FIG. 9 shows an example embodiment of the arrangement of the scattered radiation grid 3, scintillator unit 5 and evaluation unit 9 according to the invention in a third embodiment. A plurality of evaluation units 9 of a detection unit 7 formed by the scintillator unit 5 and scattered radiation grid 3 is assigned in the phi-direction 44.

Figure 10:
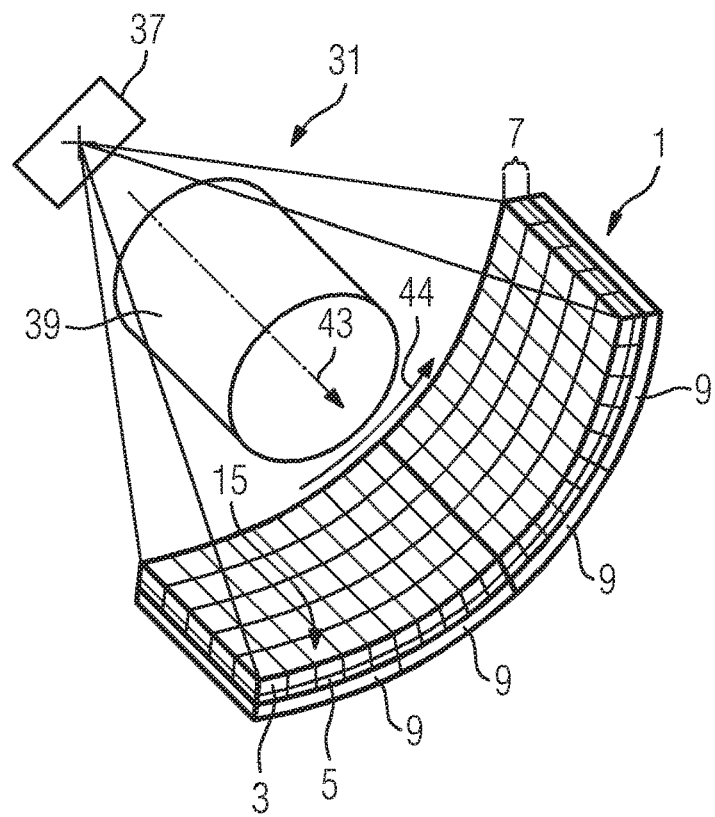
FIG. 10 a schematic view of a depiction of a computed tomography scanner according to the invention in a first embodiment.

FIG. 10 shows a first example embodiment of the computed tomography scanner 31 according to the invention in a first embodiment. The detector apparatus 1 comprises, for example, two detection units 7 with a scintillator unit 5 and scattered radiation grid 3. Each detection unit 7 is, for example, assigned two evaluation units 9. The detection units 7 and the evaluation units 9 are each arranged along the phi-axis 44. The radiation source 37 emits X-rays that are attenuated through the patient 39. The patient 39 is arranged along the direction of rotation 43.

Figure 11:
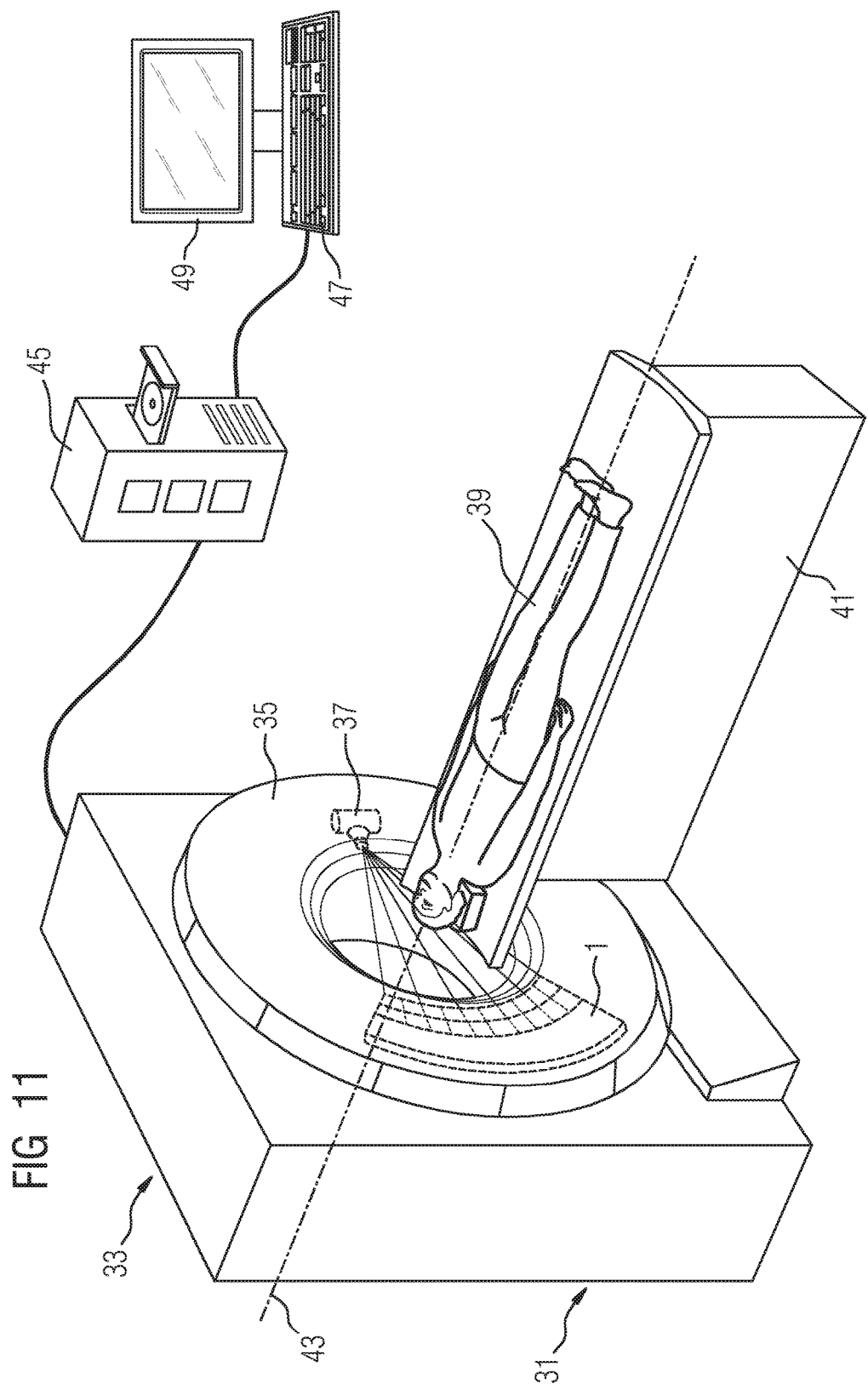
FIG. 11 a schematic view of a depiction of a computed tomography scanner according to the invention in a second embodiment.

FIG. 11 shows an example embodiment of the computed tomography scanner 31 according to the invention with a detector apparatus according to the invention 1. The detector apparatus 1 can comprise a plurality of detector modules comprising at least one X-ray detector. The detector modules preferably comprise a plurality of X-ray detectors in a two-dimensional matrix or arrangement. The computed tomography scanner 31 contains a gantry 33 with a rotor 35. The rotor 35 comprises an X-ray source 37 and the detector apparatus according to the invention 1. The patient 39 is mounted on the patient bed 41 and can be moved along the axis of rotation z 43 through the gantry 33. A computing unit 45 is used to control and calculate the sectional views. An input appliance 47 and an output apparatus 49 are connected to the computing unit 45.

Although the invention was described in more detail by the preferred example embodiments, the invention is not restricted by the examples disclosed and other variations can be derived herefrom by the person skilled in the art without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detector apparatus, comprising:
a scattered radiation grid;
a scintillator unit configured to convert X-rays into a light quantity;
an evaluation unit configured to convert the light quantity into electric signals; and
a module-receiving appliance,
the scintillator unit and the scattered radiation grid being mechanically connected to a first surface of the module-receiving appliance via a first connection,
the evaluation unit being mechanically connected to the first surface of the module-receiving appliance via a second connection, independent of the first connection, and
the evaluation unit, the scintillator unit and the scattered radiation grid being aligned with respect to one another such that the light quantity, when emitted from sub-regions of the scintillator unit, is registered by sub-regions of the evaluation unit,
wherein the first connection and the second connection are configured to be detachable, and
wherein the scintillator unit and the evaluation unit define a gap therebetween.

2. The detector apparatus of claim 1, wherein the scintillator unit forms a detection unit with the scattered radiation grid.

3. The detector apparatus of claim 1, further comprising:
a detection unit, the detection unit and the evaluation unit having different two-dimensional extensions.

4. The detector apparatus of claim 1, further comprising:
a detection unit assigned to a plurality of evaluation units.

5. The detector apparatus of claim 1, wherein one sub-region of the sub-regions of the scintillator unit is assigned to a cell of the scattered radiation grid.

6. The detector apparatus of claim 5, wherein the one sub-region of the sub-regions of the scintillator unit and the cell of the scattered radiation grid have the same two-dimensional extension.

7. The detector apparatus of claim 5, wherein the one sub-region of the sub-regions of the scintillator unit is formed in a grid opening of the scattered radiation grid.

8. The detector apparatus of claim 5, wherein the one sub-region of the sub-regions of the scintillator unit comprises a plurality of needle-shaped scintillator elements.

9. A medical device, comprising:
the detector apparatus of claim 5.

10. The medical device of claim 9, wherein the medical device is a computed tomography scanner.

11. The detector apparatus of claim 1, wherein the defined gap is filled with a fluid.

12. The detector apparatus of claim 1, wherein the defined gap is filled with an optical filler.

13. A medical device, comprising:
the detector apparatus of claim 1.

14. The medical device of claim 13, wherein the medical device is a computed tomography scanner.

15. The detector apparatus of claim 1, wherein the scintillator unit forms a detection unit with the scattered radiation grid.

16. The detector apparatus of claim 1, wherein the detection unit and the evaluation unit have different two-dimensional extensions.

17. The detector apparatus of claim 1, wherein the detection unit is assigned to a plurality of evaluation units.

18. The detector apparatus of claim 1, wherein one sub-region of the sub-regions of the scintillator unit is assigned to a cell of the scattered radiation grid.

* * * * *